(12) United States Patent  
Mitchell (10) Patent No.: US 9,298,078 B2  
(45) Date of Patent: Mar. 29, 2016

(54) METHOD AND APPARATUS FOR GENERATING THREE-DIMENSIONAL IMAGE INFORMATION USING A SINGLE IMAGING PATH

(75) Inventor: Thomas N. Mitchell, Bowen Island (CA)

(73) Assignee: STEROPES TECHNOLOGIES, LLC, Pensacola, FL (US)

( * ) Notice: Subject to any disclaimer, the term of this patent is extended or adjusted under 35 U.S.C. 154(b) by 1030 days.

(21) Appl. No.: 13/382,895

(22) PCT Filed: Jul. 10, 2009

(86) PCT No.: PCT/CA2009/000957  
§ 371 (c)(1),  
(2), (4) Date: Feb. 27, 2012

(87) PCT Pub. No.: WO2011/003168  
PCT Pub. Date: Jan. 13, 2011

(65) Prior Publication Data  
US 2012/0188347 A1   Jul. 26, 2012

(51) Int. Cl.  
*H04N 13/02* (2006.01)  
*G03B 35/04* (2006.01)  
(Continued)

(52) U.S. Cl.  
CPC ............ *G03B 35/04* (2013.01); *A61B 1/00193* (2013.01); *A61B 1/04* (2013.01); *G03B 35/02* (2013.01); *H04N 13/021* (2013.01); *H04N 13/0217* (2013.01)

(58) Field of Classification Search  
CPC ...... A61B 1/00193; A61B 1/04; G03B 35/04; H04N 13/021; H04N 13/0217  
See application file for complete search history.

(56) References Cited

U.S. PATENT DOCUMENTS

| | | |
|---|---|---|
| 2,255,631 A | 9/1941 | Schulman |
| 3,464,766 A | 9/1969 | Knauf |

(Continued)

FOREIGN PATENT DOCUMENTS

| | | |
|---|---|---|
| CA | 2177165 A1 | 6/1995 |
| CA | 2457506 A1 | 3/2003 |

(Continued)

OTHER PUBLICATIONS

Anonymous. (Jun. 1993)."3-D Imaging For Minimally Invasive Surgery gets MDs' Attention," *Health Technology Trends* 5(6):4-5.

(Continued)

*Primary Examiner* — Christopher S Kelley  
*Assistant Examiner* — Asmamaw G Tarko  
(74) *Attorney, Agent, or Firm* — Morrison & Foerster LLP (57) ABSTRACT

A method and apparatus for generating three dimensional image information using a single imaging path having an associated field of view. Two images are selectively received through respective portions of the single imaging path, each portion having a perspective viewpoint within the field of view. The two images together are operable to represent three dimensional spatial attributes of objects within the field of view. To create a change in the representation of the three dimensional spatial attributes, an extent of the two portions of the imaging path are varied to cause the perspective viewpoints to change location. While varying the extent of the portions, compensating for changes in transmission allows an image intensity associated with each of the two images to be maintained at a generally uniform image intensity level.

17 Claims, 7 Drawing Sheets

(51) Int. Cl.
  *A61B 1/00* (2006.01)
  *A61B 1/04* (2006.01)
  *G03B 35/02* (2006.01)

(56) References Cited

U.S. PATENT DOCUMENTS

| | | | |
|---|---|---|---|
| 3,712,199 | A | 1/1973 | Songer, Jr. |
| 3,784,291 | A | 1/1974 | Hirata et al. |
| 3,825,328 | A * | 7/1974 | Hoch ............... 352/60 |
| 4,021,846 | A | 5/1977 | Roese |
| 4,059,336 | A | 11/1977 | Hopkins |
| 4,103,260 | A * | 7/1978 | Buchman ............... 359/250 |
| 4,196,966 | A | 4/1980 | Malis |
| 4,303,316 | A | 12/1981 | McElveen |
| 4,392,710 | A | 7/1983 | Rogers |
| 4,568,160 | A | 2/1986 | Krueger |
| 4,601,552 | A | 7/1986 | Jessmore |
| 4,651,201 | A | 3/1987 | Schoolman |
| 4,761,066 | A | 8/1988 | Carter |
| 4,924,853 | A | 5/1990 | Jones, Jr. et al. |
| 5,059,009 | A | 10/1991 | McKinley |
| 5,094,523 | A | 3/1992 | Reznichenko et al. |
| 5,097,359 | A | 3/1992 | McKinley |
| 5,122,650 | A | 6/1992 | McKinley |
| 5,222,477 | A | 6/1993 | Lia |
| 5,471,237 | A | 11/1995 | Shipp |
| 5,532,777 | A | 7/1996 | Zanen |
| 5,588,948 | A | 12/1996 | Takahashi et al. |
| 5,671,450 | A | 9/1997 | Suzuki |
| 5,703,677 | A | 12/1997 | Simoncelli et al. |
| 5,720,706 | A | 2/1998 | Takahashi |
| RE35,816 | E | 6/1998 | Schulz |
| 5,828,487 | A | 10/1998 | Greening et al. |
| 5,835,133 | A | 11/1998 | Moreton et al. |
| 6,006,001 | A | 12/1999 | Alfano et al. |
| 6,151,164 | A | 11/2000 | Greening et al. |
| 6,275,335 | B1 | 8/2001 | Costales |
| 6,348,994 | B1 | 2/2002 | Geier et al. |
| 6,359,664 | B1 | 3/2002 | Faris |
| 6,400,394 | B1 | 6/2002 | Kim et al. |
| 6,546,208 | B1 | 4/2003 | Costales |
| 6,624,935 | B2 | 9/2003 | Weissman et al. |
| 6,683,716 | B1 | 1/2004 | Costales |
| 7,324,279 | B2 | 1/2008 | Penn |
| 7,683,926 | B2 | 3/2010 | Schechterman et al. |
| 7,978,892 | B2 | 7/2011 | Quadling et al. |
| 2002/0118453 | A1 * | 8/2002 | Geier et al. ............... 359/465 |
| 2002/0131170 | A1 | 9/2002 | Costales |
| 2007/0064163 | A1 * | 3/2007 | Tan et al. ............... 349/5 |
| 2007/0132953 | A1 | 6/2007 | Silverstein |
| 2007/0165305 | A1 * | 7/2007 | Mehrle ............... 359/464 |
| 2007/0188863 | A1 | 8/2007 | Sun et al. |
| 2008/0204663 | A1 * | 8/2008 | Balogh ............... 353/10 |
| 2008/0204754 | A1 * | 8/2008 | Martinez ............... 356/436 |
| 2008/0239135 | A1 | 10/2008 | Tamura |
| 2009/0219595 | A1 * | 9/2009 | Olaya et al. ............... 359/25 |
| 2009/0284708 | A1 * | 11/2009 | Abdulhalim ............... 349/198 |
| 2011/0316975 | A1 * | 12/2011 | Tan ............... 348/46 |
| 2012/0056996 | A1 * | 3/2012 | Sander et al. ............... 348/47 |
| 2013/0038690 | A1 * | 2/2013 | Mitchell et al. ............... 348/46 |

FOREIGN PATENT DOCUMENTS

| | | |
|---|---|---|
| CA | 2545418 A1 | 5/2005 |
| WO | WO-95/14952 A1 | 6/1995 |
| WO | WO-97/03378 A1 | 1/1997 |
| WO | WO-01/91472 A2 | 11/2001 |
| WO | WO-01/91472 A3 | 11/2001 |

OTHER PUBLICATIONS

Chinese Office Action mailed on Dec. 25, 2013, for Chinese Patent Application No. 201080040644.3, 30 pages. (with English translation).

International Search Report mailed on Sep. 21, 2010, for PCT Patent Application No. PCT/CA2010/001093, filed on Jul. 12, 2010, 10 pages.

International Search Report mailed on Mar. 18, 2010, for PCT Patent Application No. PCT/CA2009/000957, filed on Jul. 10, 2009, 7 pages.

Mitchell, T.N. et al. (Oct. 1993). "Three-Dimensional Endoscopic Imaging for Minimal Access Surgery," *JR Coll Surg Edinb* 38(5): 285-292.

Nagy, A.G. et al. (1993). "The Future: Telepresence and Other Developments Minimally Invasive Surgery in Gastro-Intestinal Cancer" Chapter 12 in *Minimally Invasive Surgery in Gastrointestinal Cancer*, published by Churchill Livingstone, pp. 171-184.

Nagy, A.G. et al. (Mar. 1994). "New Technologies in Laparoscopic Surgery," *BC Medical Journal* 36(3):179-183.

Written Opinion mailed on Sep. 21, 2010, for PCT Patent Application No. PCT/CA2010/001093, filed on Jul. 12, 2010, 5 pages.

Written Opinion mailed on Mar. 18, 2010, for PCT Patent Application No. PCT/CA2009/000957, filed on Jul. 10, 2009, 4 pages.

* cited by examiner

METHOD AND APPARATUS FOR GENERATING THREE-DIMENSIONAL IMAGE INFORMATION USING A SINGLE IMAGING PATH

CROSS REFERENCE TO RELATED APPLICATIONS

This application is a National Phase filing under 35 U.S.C. §371 of International Application PCT/CA2009/000957, with an International Filing Date of Jul. 10, 2009, entitled "METHOD AND APPARATUS FOR GENERATING THREE-DIMENSIONAL IMAGE INFORMATION USING A SINGLE IMAGING PATH, which is hereby incorporated by reference in its entirety and for all purposes as if put forth in full below.

BACKGROUND OF THE INVENTION

1. Field of Invention

This invention relates generally to generating three dimensional image information and more particularly to generating three dimensional image information using a single imaging path.

2. Description of Related Art

Imaging generally involves producing a representation of a scene by receiving radiation emitted or reflected by objects in the scene at a suitable image sensor. Some examples of radiation that may be imaged include visible light, infrared light or heat, radiofrequency waves, acoustic waves, and ultrasonic waves.

A three-dimensional (3D) scene includes depth information, which in many imaging systems is mapped onto a two-dimensional (2D) image plane and is thus not preserved. A conventional camera is an example of an optical imaging system in which depth information is not preserved resulting in a 2D image representing the scene. Stereoscopic optical systems are capable of producing images that represent depth information by producing separate images from differing perspective viewpoints. The depth information may be used to produce 3D measurements between points in the scene, for example. Alternatively, the separate images may be presented to respective left and right eyes of a user to enable the user to perceive an image view having at least some depth represented in the images. The stereoscopic system thus produces images having spatially separated perspective viewpoints that mimic the operation of the human eyes in viewing a real scene. The images may be viewed using some form of active eyewear or by operating a display to project spatially separated images toward the user's respective left and right eyes.

The use of stereoscopic imaging finds application in surgery where a 3D endoscope may be used to provide a 3D view to the surgeon. Stereoscopic imaging may also be useful in remote operations, such as undersea exploration for example, where control of a robotic actuator is facilitated by providing 3D image information to an operator who is located remotely from the actuator. Other applications of stereoscopic imaging may be found in physical measurement systems and in the entertainment industry.

SUMMARY OF THE INVENTION

In accordance with one aspect of the invention there is provided a method of generating three dimensional image information using a single imaging path having an associated field of view. The method involves selectively receiving first and second images through respective first and second portions of the single imaging path, the first portion having a first perspective viewpoint within the field of view and the second portion having a second perspective viewpoint within the field of view. The first and second images together are operable to represent three dimensional spatial attributes of objects within the field of view. The method also involves varying an extent of the first and second portions of the imaging path to cause the first and second perspective viewpoints to change location while receiving the first and second images, the change in perspective viewpoint location providing a corresponding change in the representation of the three dimensional spatial attributes. The method further involves compensating for changes in transmission through the first and second portions of the imaging path such that while varying the extent of the first and second portions, an image intensity associated with each of the first and second images is maintained at a generally uniform image intensity level.

Selectively receiving the first and second images may involve receiving the first and second images at an image sensor and compensating for the changes in the transmission may involve one of increasing an exposure associated with the image sensor in response to a reducing extent of the first and second portions of the imaging path, decreasing a gain associated with the image sensor in response to an increasing extent of the first and second portions of the imaging path, increasing overall transmittance through the imaging path in response to a reducing extent of the first and second portions of the imaging path, and reducing overall transmittance through the imaging path in response to an increasing extent of the first and second portions of the imaging path.

Selectively receiving the first and second images may involve alternately blocking the first portion of the imaging path while receiving the second image, and blocking the second portion of the imaging path while receiving the first image.

Alternately blocking the first and second portions of the imaging path may involve causing a blocking element located proximate an aperture plane of the image path to move between first and second positions in the image path to define the varying extent of the first and second portions of the imaging path.

Causing the blocking element to move may involve producing a force operable to alternately move the blocking element toward one of the first and second positions, receiving a position signal representing a position of the blocking element, and controlling a magnitude of the force in response to the position signal to cause the blocking element to come to rest at the one of the first and second positions.

Alternately blocking the first and second portions of the imaging path may involve selectively actuating first and second regions of an optical element located proximate an aperture plane of the image path to selectively block the first and second portions of the imaging path.

The optical element may involve a plurality of elements and selectively actuating the first and second regions may involve selectively actuating one of a first plurality of elements in the plurality of elements, and a second plurality of elements in the plurality of elements.

Each element of the plurality of elements may be operable to be actuated in response to receiving an actuation signal, and varying the extent of the first and second portions of the imaging path may involve generating actuation signals to cause a number of elements in the first and second plurality of elements to be selectively varied to vary the extent of the first and second portions of the imaging path.

Selectively actuating the first and second regions of the optical element may involve selectively actuating first and second regions of a transmissive optical element disposed to transmit light through the respective first and second portions of the single imaging path.

Selectively actuating first and second regions of the transmissive optical element may involve selectively actuating first and second regions of one of a liquid crystal element, and a light valve.

Selectively actuating the first and second regions of the optical element may involve selectively actuating first and second regions of a reflective optical element disposed to reflect light through the respective first and second portions of the single imaging path.

Selectively actuating first and second regions of the reflective optical element may involve selectively actuating first and second regions of a light valve having a plurality of moveable mirror elements.

Selectively receiving the first and second images may involve simultaneously receiving a first image having first image attributes and a second image having second image attributes, and separating the first and second images in accordance with the first and second image attributes to produce respective first and second image representations.

Receiving the first image may involve receiving a first image having a first state of polarization and receiving the second image may involve receiving a second image having a second state of polarization, and separating the first and second images may involve receiving the first and second images at a sensor array having a first plurality of elements responsive to radiation of the first polarization state and a second plurality of elements responsive to radiation of the second polarization state.

The method may involve generating the first image having the first state of polarization and generating the second image having the second state of polarization.

Varying the extent may involve varying the extent of the first and second portions of the imaging path in response to a control signal.

The method may involve generating the control signal.

A location of the first perspective viewpoint may be defined by a first centroid location and a location of the second perspective viewpoint may be defined by a second centroid location, and generating the control signal may involve generating a control signal operable to cause the first and second centroids to move with respect to each other at a generally constant rate to provide a smooth change in the representation of the three dimensional spatial attributes.

A location of the first perspective viewpoint may be defined by a first centroid location and a location of the second perspective viewpoint is defined by a second centroid location, and varying the extent may involve varying the extent of the first and second portions of the imaging path between a first extent where the first and second centroid locations may be proximally located causing the first and second images to may include predominately two-dimensional spatial attributes within the field of view, and a second extent where the first and second centroid locations are spaced apart to cause the first and second images to may include an increasing degree of three dimensional spatial attribute information.

Varying the extent of the first and second portions of the imaging path may involve varying the extent to provide a smooth transition from one of the first extent to the second extent to produce a two-dimensional to three-dimensional transition effect, and the second extent to the first extent to produce a three-dimensional to two-dimensional transition effect.

Receiving the first and second images may involve sequentially receiving a plurality first and second images representing time variations of subject matter within the field of view.

In accordance with another aspect of the invention there is provided an apparatus for generating three dimensional image information using a single imaging path having an associated field of view. The apparatus includes provisions for selectively receiving first and second images through respective first and second portions of the single imaging path, the first portion having a first perspective viewpoint within the field of view and the second portion having a second perspective viewpoint within the field of view, the first and second images together being operable to represent three dimensional spatial attributes of objects within the field of view. The apparatus also includes provisions for varying an extent of the first and second portions of the imaging path to cause the first and second perspective viewpoints to change location while receiving the first and second images, the change in perspective viewpoint location providing a corresponding change in the representation of the three dimensional spatial attributes. The apparatus further includes provisions for compensating for changes in transmission through the first and second portions of the imaging path such that while varying the extent of the first and second portions, an image intensity associated with each of the first and second images is maintained at a generally uniform image intensity level.

In accordance with another aspect of the invention there is provided an apparatus for generating three dimensional image information. The apparatus includes a single imaging path having an associated field of view. The apparatus also includes an image modulator operably configured to cause first and second images to be selectively received through respective first and second portions of the single imaging path, the first portion having a first perspective viewpoint within the field of view and the second portion having a second perspective viewpoint within the field of view. The first and second images together are operable to represent three dimensional spatial attributes of objects within the field of view. The apparatus also includes a controller in communication with the modulator, the controller being operably configured to produce a signal operable to cause the modulator to vary an extent of the first and second portions of the imaging path to cause the first and second perspective viewpoints to change location while receiving the first and second images, the change in perspective viewpoint location providing a corresponding change in the representation of the three dimensional spatial attributes. The apparatus further includes a compensator operably configured to compensate for changes in transmission through the first and second portions of the imaging path such that while varying the extent of the first and second portions, an image intensity associated with each of the first and second images is maintained at a generally uniform image intensity level.

The single imaging path may be operably configured to produce the first and second images at an image sensor and the compensator may be operably configured to compensate for the changes in the transmission by one of increasing an exposure associated with the image sensor in response to a reducing extent of the first and second portions of the imaging path, decreasing an exposure associated with the image sensor in response to an increasing extent of the first and second portions of the imaging path, increasing overall transmittance through the imaging path in response to a reducing extent of the first and second portions of the imaging path, and reducing overall transmittance through the imaging path in response to an increasing extent of the first and second portions of the imaging path.

The modulator may be operably configured to alternately block the first portion of the imaging path while receiving the second image, and block the second portion of the imaging path while receiving the first image.

The modulator may be operably configured to cause a blocking element located proximate an aperture plane of the image path to move between first and second positions in the image path to define the varying extent of the first and second portions of the imaging path.

The modulator may include an actuator for producing a force operable to alternately move the blocking element toward one of the first and second positions, a position sensor operably configured to produce a position signal representing a position of the blocking element, and the controller may be operably configured to control a magnitude of the force in response to the position signal to cause the blocking element to come to rest at the one of the first and second positions.

The modulator may include an optical element having first and second regions, the first and second regions being operably configured to be selectively actuated to selectively block the first and second portions of the imaging path.

The optical element may include a plurality of elements and the first region may include a first plurality of elements and the second region may include a second plurality of elements, the first and second pluralities being selected to vary the extent of the first and second portions of the imaging path.

Each element of the plurality of elements may be operable to be actuated in response to receiving an actuation signal, and may further include a modulator driver operably configured to generate the actuation signals to cause a number of elements in the first and second plurality of elements to be selectively varied to vary the extent of the first and second portions of the imaging path.

The modulator may be operably configured to selectively actuating first and second regions of a transmissive optical element disposed to transmit light through the respective first and second portions of the single imaging path.

The modulator may include of one of a liquid crystal element, and a light valve.

The modulator may be operably configured to selectively actuate first and second regions of a reflective optical element disposed to reflect light received through the respective first and second portions of the single imaging path.

The modulator may include a light valve having a plurality of moveable mirror elements.

The modulator may be operably configured to simultaneously receive a first image having first image attributes and a second image having second image attributes, and separate the first and second images in accordance with the first and second image attributes to produce respective first and second image representations.

The modulator may include a polarizer having first and second polarization regions operably configured to generate a first image having a first state of polarization and the second image having a second state of polarization, and may further include a sensor array having a first plurality of elements responsive to radiation of the first polarization state and a second plurality of elements responsive to radiation of the second polarization state, the sensor array being operable to separate the first and second images.

The modulator may be operably configured to varying the extent of the first and second portions of the imaging path in response to a control signal.

The controller may be operably configured to generate the control signal.

A location of the first perspective viewpoint may be defined by a first centroid location and a location of the second perspective viewpoint is defined by a second centroid location, and the controller is operably configured to generate the control signal by generating a control signal operable to cause the first and second centroids to move with respect to each other at a generally constant rate to provide a smooth change in the representation of the three dimensional spatial attributes.

A location of the first perspective viewpoint may be defined by a first centroid location and a location of the second perspective viewpoint is defined by a second centroid location, and the modulator is operably configured to vary the extent of the first and second portions of the imaging path between a first extent the first and second centroid locations may be proximally located causing the first and second images to may include predominately two-dimensional spatial attributes within the field of view, and a second extent the first and second centroid locations are spaced apart to cause the first and second images to may include an increasing degree of three dimensional spatial attribute information.

The modulator may be operably configured to vary the extent of the first and second portions of the imaging path by varying the extent to provide a smooth transition from one of the first extent to the second extent to produce a two-dimensional to three-dimensional transition effect, and the second extent to the first extent to produce a three-dimensional to two-dimensional transition effect.

The image path may be operably configured to receiving the first and second images by sequentially receiving a plurality first and second images representing time variations of subject matter within the field of view.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
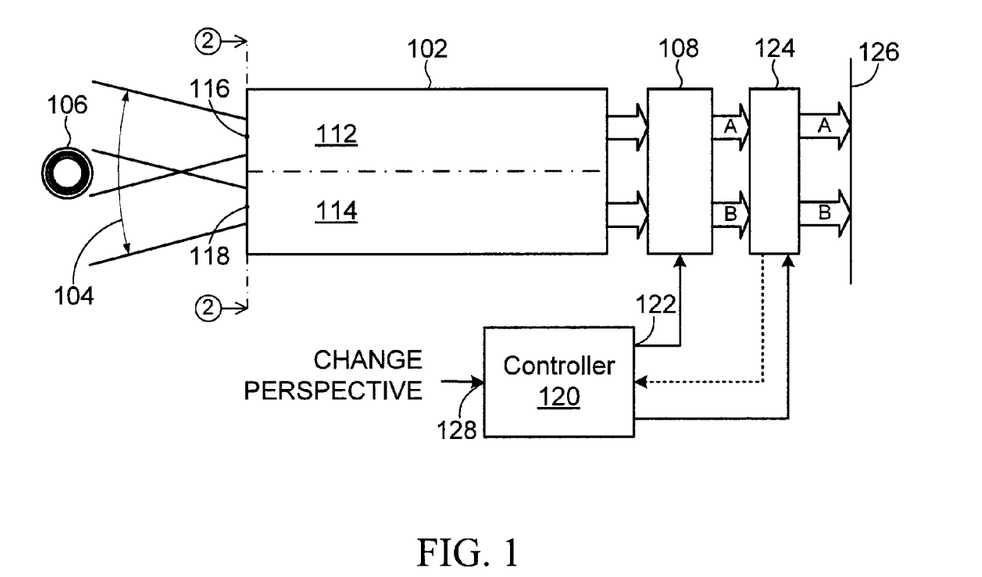
FIG. 1 is a top schematic view of an apparatus for generating three-dimensional image information in accordance with a first embodiment of the invention.

Referring to FIG. 1, an apparatus according to a first embodiment of the invention for generating three-dimensional image information is shown in schematic top view generally at 100. The apparatus 100 includes a single imaging path 102 having an associated field of view 104, which in this embodiment includes an object 106. The apparatus 100 also includes an image modulator 108 operably configured to cause first and second images (shown schematically as "A" and "B" in FIG. 1) to be selectively received through respective first and second portions 112 and 114 of the single imaging path 102.

Figure 2:
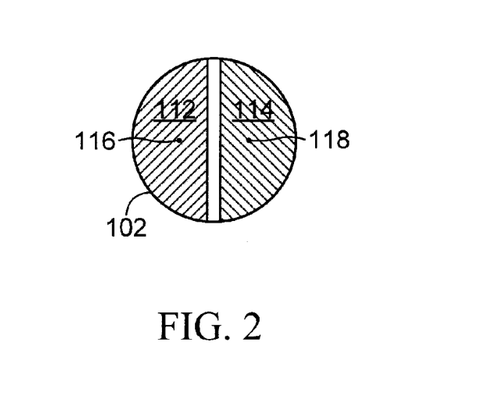
FIG. 2 is a front schematic view of an imaging path of the apparatus shown in FIG. 1.

Referring to FIG. 2, in this embodiment the imaging path is circular and the first and second portions 112 and 114 each generally comprise a circular segment. The first portion 112 defines a first perspective viewpoint within the field of view 104, which is represented by a first centroid 116. The second portion 114 defines a second perspective viewpoint within the field of view 104, which is represented by a second centroid 118. In other embodiments the imaging path may be non-circular.

The apparatus 100 also includes a controller 120 in communication with the modulator 108. The controller 120 includes an output 122 for producing a control signal operable to cause the modulator 108 to vary an extent of the first and second portions 112 and 114 of the imaging path, thereby causing the first and second perspective viewpoints 116 and 118 to change location while receiving the first and second images. The change in location of perspective viewpoints 116 and 118 provides a corresponding change in the representation of the three dimensional spatial attributes the object 106 within the field of view 104.

The apparatus 100 also includes a compensator 124. The compensator 124 is operably configured to compensate for changes in transmission through the first and second portions 112 and 114 of the imaging path 102 such that while varying the extent of the first and second portions, an image intensity associated with each of the first and second images A and B is maintained at a generally uniform image intensity level.

The first and second images A and B are formed at an image plane 126, and together the first and second images are operable to represent three dimensional spatial attributes the object 106, and other objects within the field of view 104. In this embodiment the controller 120 also includes an input 128 for receiving user input of a desired change in perspective and the controller is operably configured to produce the control signal at the output 122 in response to the user input.

In one embodiment the imaging path 102 may be an optical imaging path operable to receive light radiation for producing the images. The light radiation may have a wavelength range in the infrared, visible, and/or ultra-violet wavelength ranges. In other embodiments the imaging path 102 may be operable to produce images in response to receiving acoustic, ultrasonic, or radio frequency signals. The image at the image plane 126 may be captured by any suitable image capture device using any of a variety of recording methods and/or media. For example, the image capture device may be a still camera or movie camera having a photosensitive film or a charge coupled device (CCD) array for recording the images. Alternatively, a piezoelectric crystal array may be used for acoustic or ultrasonic imaging, and an antenna or antenna array may be used for radio frequency imaging, for example.

Advantageously, the single image path 102 produces A and B images from which 3D information can be perceived and/or extracted without requiring any special alignments other than would normally be required in assembling the image path. In contrast, when using separate image paths or an image path that optically divides into two spaced apart image paths, there is a significant alignment challenge and any minor misalignment may cause eyestrain or other uncomfortable effects for users.

Optical Imaging Embodiment

Figure 3:
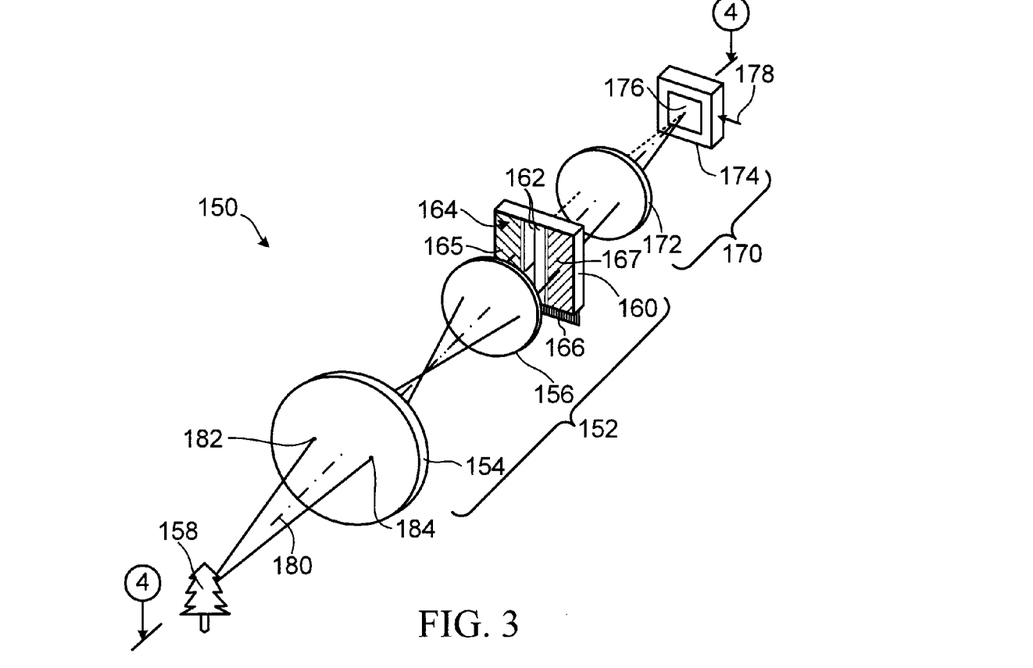
FIG. 3 is a perspective view of an optical imaging apparatus for generating three-dimensional image information in accordance with another embodiment of the invention.

Referring to FIG. 3, an optical imaging apparatus embodiment for generating three-dimensional image information is shown generally at 150. The optical imaging apparatus 150 includes a single imaging path 152, having a first lens 154 and a second lens 156 disposed to receive light rays from an object 158 within a field of view of the first and second lenses.

The optical imaging apparatus 150 also includes a liquid crystal device (LCD) modulator 160 having a plurality of elements 162. Each element 162 defines a columnar portion of a front surface area 164 of the modulator 160 that may be selectively controlled to alternately block a first portion 165 of the imaging path 152 while receiving a first image, and a second portion 167 of the imaging path while receiving a second image. The modulator 160 also includes a plurality of control inputs 166, each element 162 having an associated control input for receiving an actuation signal for selectively actuating the element.

The optical imaging apparatus 150 further includes a camera 170 having a third lens 172 and a CCD image sensor 174 located at an image plane of the camera 170. The camera may be a still camera or a video camera and may be sensitive to visible or non-visible light. The third lens 172 gathers light transmitted by the modulator 160 and forms an image on the image sensor 174. The image sensor 174 includes a photosensitive area 176, and one or more control inputs 178 for receiving various control signals operable to control operations of the sensor related to capturing the image. In general the image sensor 174 has a spatial array of photosensitive elements that accumulate charges in proportion to incident light on the element. The accumulated charge may be read out of the image sensor 174 by serially shifting the charges through adjacent coupled elements to a charge amplifier, which converts the charges into a voltage signal representing the light incident on the associated element. In another embodiment, the image sensor 174 may be a complementary metal-oxide-semiconductor (CMOS) active-pixel sensor, or other electronic image sensor. Alternatively, the image sensor 174 may be a photosensitive film emulsion, such as 35 mm film for example.

The image sensor 174, third lens 172, liquid crystal modulator 160, first lens 154, second lens 156, and the camera 170 are all aligned along an optical axis 180.

Figure 4:
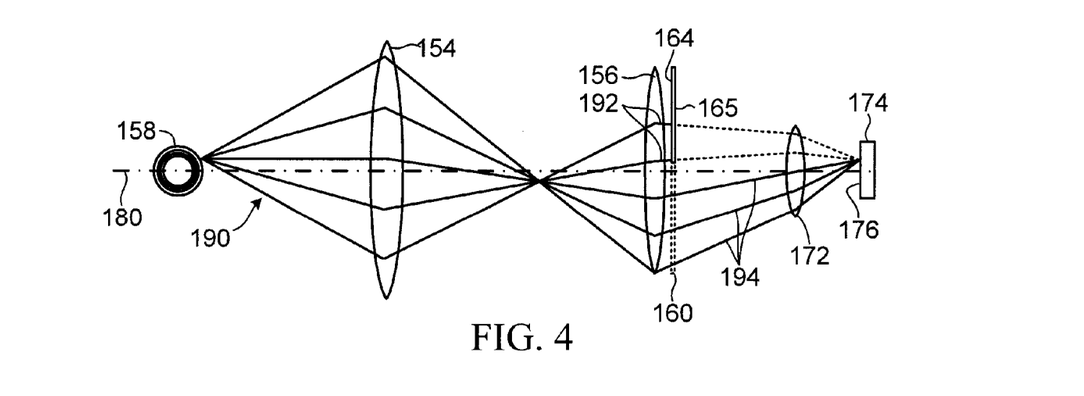
FIG. 4 is a cross-sectional view of the optical imaging apparatus shown in FIG. 3, taken along the line 4-4.

The apparatus 150 is shown in cross section in FIG. 4, with the imaging path 152 being illuminated by a bundle or cone of rays 190 emanating from an off-axis point on the object 158. In general, for an optical system such as that shown in FIG. 3 and FIG. 4, a diameter of one of the optical elements will limit which rays in the bundle 190 can pass through the optical system, and this diameter defines the system aperture. The image of the system aperture by optical surfaces located between the aperture and the object 158 defines a location and extent of an entrance pupil for the system. The entrance pupil in turn defines a bundle of rays that are able to pass through the imaging path. In this case, it will be assumed that the first lens 154 is the system aperture and thus also the entrance pupil and 152 rays that impinge on the first lens will be transmitted through the imaging path through the imaging path 152. In other embodiments, the entrance pupil may be located in front of or behind the first lens 154, depending on the configuration of the lenses.

Rays in the bundle 190 that enter the first lens 154 are thus focused through the second lens 156 and impinge on the front surface area 164 of the modulator 160. When a partial occlusion such as the actuated first portion 165 of the modulator 160 is located after the system aperture in the imaging path 152, vignetting of the image occurs. In this case, rays 192 in the bundle of rays 190 are blocked by the first portion 165 of the front surface area 164 of the modulator 160 and do not reach the photo-sensitive area 176 of the sensor 174. Rays 194 in the bundle of rays 190 pass through the modulator 160, and are focused onto the photo-sensitive area 176 by the lens 172. Vignetting reduces the overall illumination of the image formed at the photo-sensitive area 176 of the sensor 174. However, since the rays 194 intersect at the photo-sensitive area 176 of the sensor 174, a real image is formed at the sensor. Furthermore the vignetting caused by the modulator does not change the angle of view at the entrance pupil.

Other points on the object 158 will be similarly imaged to produce a first image of the object 158 on the photo-sensitive area 176 of the sensor 174. The first image produced by the optical imaging apparatus 150 under the vignetting conditions shown in FIG. 4, is shown generally at 200 in FIG. 5. The image 200 corresponds to a right perspective viewpoint represented by a centroid 182 (shown in FIG. 1). Similarly, by providing control signals to the modulator 160 to cause the first portion 165 to transmit light while controlling a plurality of elements 162 on an opposite side of the modulator 160 to block light, a second image 202 (shown in FIG. 5) is produced by the apparatus 150. The second image 202 corresponds to a left perspective viewpoint represented by a centroid 184 (shown in FIG. 1).

Figure 5:
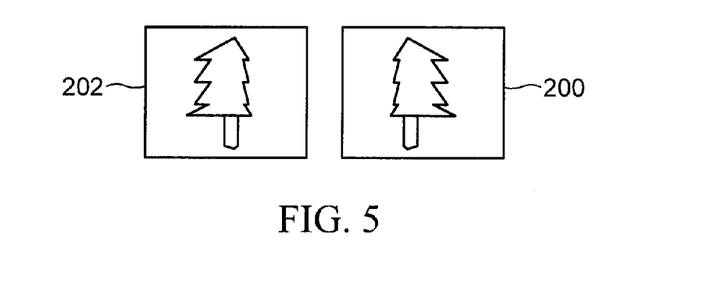
FIG. 5 is a representation of first and second images produced by the optical imaging apparatus shown in FIG. 3.

The first and second images 200 and 202 together include information representative of three dimensional spatial attributes of objects within the field of view. For example, a user separately viewing the image 200 using their right eye while viewing the image 202 using their left eye will be able to perceive a similar depth effect that would be perceptible if the user were to view the object directly. In one embodiment the images may be separately directed to the respective left and right eyes of the user using a pair of stereoscopic viewing glasses, for example.

Controller

Figure 6:
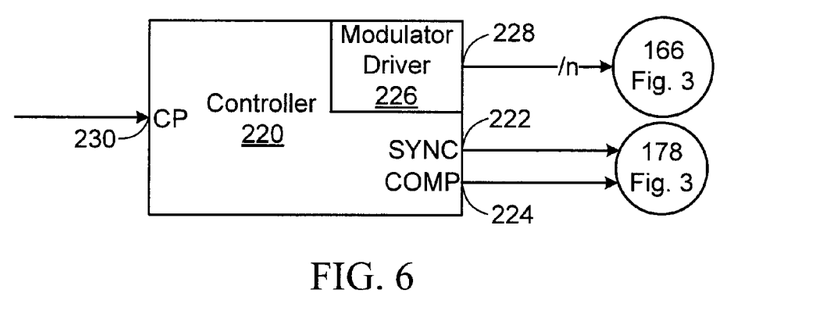
FIG. 6 is a block diagram of a controller for controlling operation of the optical imaging apparatus shown in FIG. 3.

A controller for controlling operation of the optical imaging apparatus 150 (shown in FIG. 3) is shown at 220 in FIG. 6. The controller 220 includes an output 222 for producing a synchronization signal (SYNC), which typically comprises a pulse train. The output 222 is in communication with the image sensor input 178 for synchronizing the image capture at the image sensor 174. The controller 220 also includes an output 224 for producing a compensation signal (COMP) for controlling image intensity compensation. In the embodiment shown, the output 224 is in communication with the image sensor input 178 and the image sensor acts as the compensator 124 shown in FIG. 1. In other embodiments the COMP signal produced at the output 224 may be used to control an aperture stop compensator such as an adjustable iris in the optical system to reduce or increase the bundle of rays accepted by the imaging path. Electronically controlled auto-iris diaphragms are commonly used in cameras that automatically select an aperture size and exposure to ensure correct image exposure.

The controller 220 further includes a modulator driver 226 having an output 228 for driving the control input 166 of the modulator 160. In the embodiment shown, the output 228 has "n" output channels corresponding to the number of elements 162 on the modulator 160. The controller 220 also includes an input 230 for receiving a change perspective (CP) user input. For example, the CP input 230 may be provided from a biased single-pole-double-throw switch configured to provide a varying potential at the input.

In one embodiment the controller 220 may be implemented using a processor circuit such as a micro-controller, for example.

Controller Operation

Figure 7:
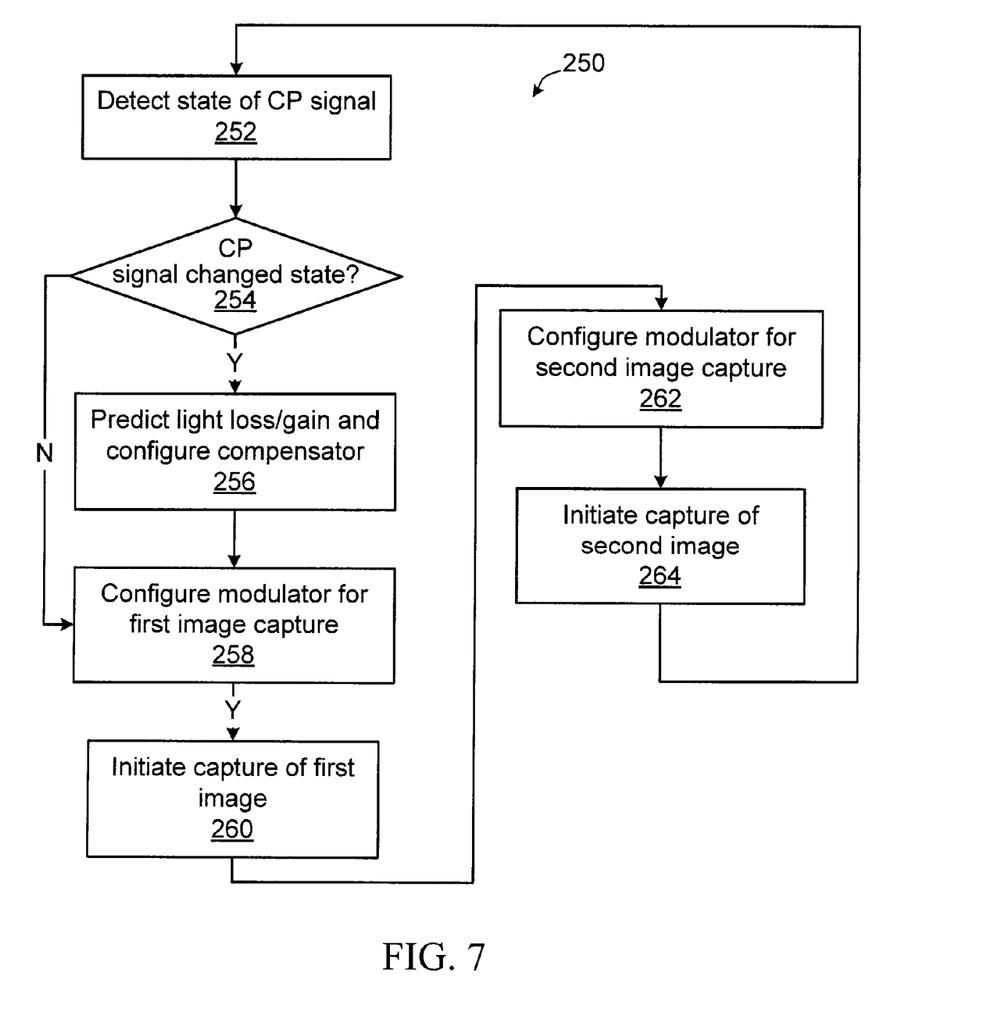
FIG. 7 is a process flow chart depicting a control process implemented by the controller shown in FIG. 6.

The operation of the controller 220 in controlling operation of the optical imaging apparatus 150 is described further with reference to FIG. 3, FIG. 6, and FIG. 7. Referring to FIG. 7, one embodiment of a control process implemented by the controller 220 is shown generally at 250.

As shown at 252, the process begins with the controller 220 detecting a signal state associated with the CP signal at the input 230. As shown at 254, if the CP signal has changed state, indicating that the user wishes to change the image perspective, then the process continues at 256.

As shown at 256, the compensator then produces a predicted light loss or gain in response to the CP signal. In embodiments where the controller 220 is implemented using a microcontroller, the predicted light loss or gain may be computed for the detected CP signal state change at the input 230. Alternatively, the predicted light loss or gain may be pre-determined and stored as a look up table in a memory of the processor circuit. The predicted light loss or gain is then used to produce a compensation signal (COMP) at the output 224 of the controller, in a format suitable for driving the particular image sensor 174. For example, in an embodiment where the image sensor 174 comprises a full frame CCD architecture, the amount of light captured by the CCD array may be controlled by a mechanical shutter (not shown) proximate the focal plane and the COMP signal would then be configured to cause the mechanical shutter to operate with a suitable shutter speed to produce a desired image intensity. Alternatively, for frame-transfer or interline transfer CCD devices, the COMP signal may be a gating signal for gating a light accumulation phase of image capture such that the CCD elements are only configured to receive light for a portion of the time between successive image captures. Some CCD sensors also permit adjustment of a gain associated either analog charge amplification and/or the analog to digital conversion of the charge signals, and this gain may also be controlled by the COMP signal to compensate for the intensity of the first and second images. The process then continues at 258.

If at 254, the CP signal has not changed state then there is no light loss/gain to compensate for and the process continues directly at 258.

As shown at 258, the modulator 160 is configured for the first image capture in accordance with the CP signal state, which involves configuring the modulator to drive a first plurality of the n-channels 228 to cause a first plurality of the elements 162 of the modulator 160 to be controlled to block light. At 260, capture of the first image is initiated when the controller produces a SYNC pulse at the output 222. The captured first image may be recorded in analog or digital format on an image storage medium (not shown) such as magnetic tape, a memory, a hard drive, or a photosensitive emulsion, for example.

As shown at 262, the modulator 160 is then configured for the second image capture, by configuring the modulator to drive a second plurality of the n-channels of the output 228 to cause a second plurality of the elements 162 of the modulator 160 to be controlled to block light. At 264, capture of the second image is initiated when the controller produces a second SYNC pulse at the output 222.

For still image capture, only a single image from each of the first and second perspective viewpoints 182 and 184 is required, and in this case the SYNC signal would produce first and second time-separated synchronization pulses. The time-separation between pulses is selected to provide sufficient time for the image sensor 174 to accumulate photons sufficient to produce an image. For capture of variations in a scene in the form of sequential video images, a frame rate may be imposed by a selected video format (e.g. 29.97 frames per second for NTSC video), in which case the SYNCH signal may comprise a plurality of pulses at time intervals of about 33.3 milliseconds, for a non-interlaced image capture. Where the image acquisition rate of a particular camera is sufficiently fast, the first and second images may be captured at time intervals of 16.7 milliseconds such each eye of the user receives the respective images at the full NTSC frame rate. When capturing successive video frames, following block 264 the process continues at block 252 and the process 250 is repeated.

A series of representations of the imaging path 152 depicting a change in perspective, are shown in FIG. 8. Referring to FIG. 8A, the imaging path 152 is depicted in end view and the centroids 182 and 184 are located on a central axis of the imaging path. Under these conditions, neither the first nor the second portions of the modulator 160 are controlled to block light and the first image (A) and the second image (B) are identical. A user viewing the respective A and B images using respective left and right eyes will perceive only a standard two-dimensional (2D) image, with no three-dimensional (3D) depth perception being possible.

Figure 8A:
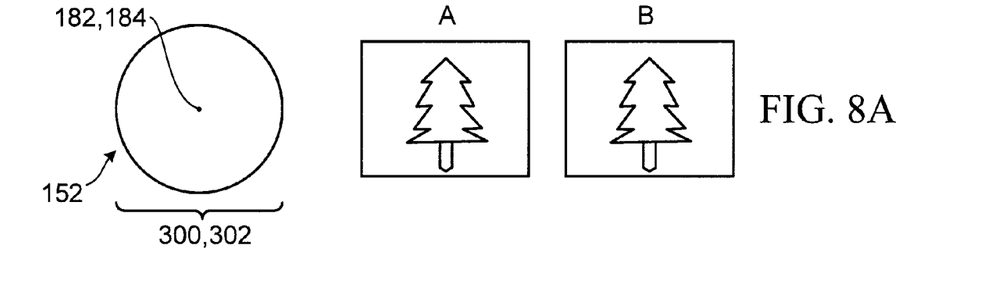
FIG. 8A-8D are a series of representations of first and second images produced by the optical imaging apparatus shown in FIG. 3.
Figure 8B:
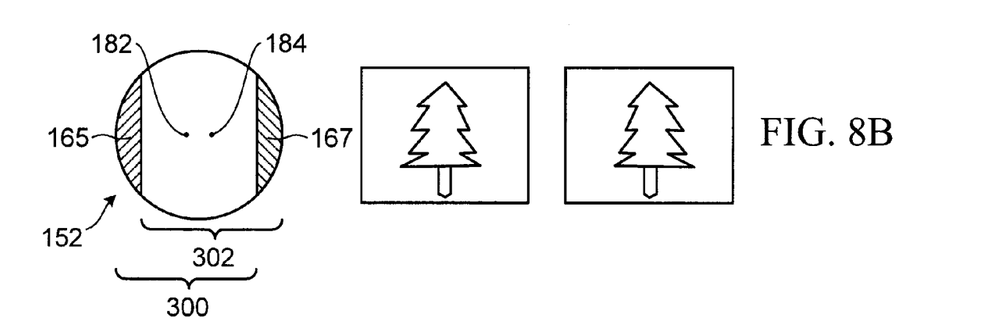

Referring to FIG. 8B, the centroids 182 and 184 have now moved outwardly and under these conditions, first and second portions 165 and 167 of the modulator 160 are alternately controlled to block light such that transmission occurs alternately through portions 300 and 302 of the imaging path 152. The resulting A and B images have slightly differing perspective viewpoints and the user viewing the respective A and B images will be able to perceive at least some 3D depth due to the differing perspectives of the images presented to each eye.

Figure 8C:
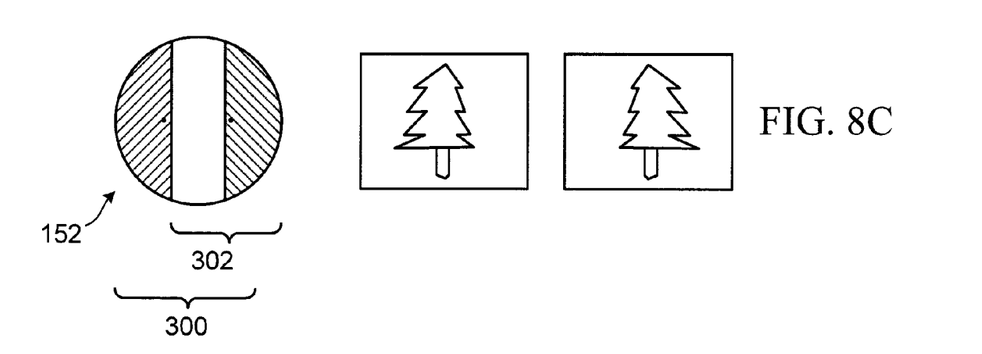

Referring to FIG. 8C, the centroids 182 and 184 have again moved further outwardly such that transmission occurs alternately through portions 300 and 302 of the imaging path 152. The resulting A and B images have greater differing perspective viewpoints than in FIG. 8B and the user viewing the respective A and B images will be able to perceive a greater degree of 3D depth.

Figure 8D:
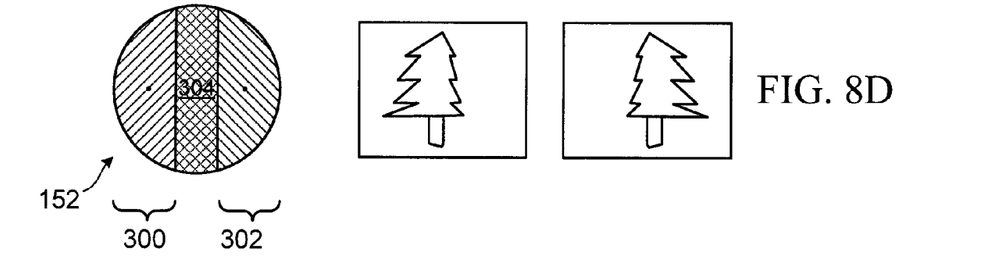

Referring to FIG. 8D, the centroids 182 and 184 are spaced apart to an extent where a region 304 of the imaging path 152 is blocked either by the first portion 165 of the modulator 160 or by the second portion 167 of the modulator. Transmission occurs alternately through the portions 300 and 302 of the imaging path 152. The resulting A and B images have even greater differing perspective viewpoints than in FIG. 8C providing and even greater degree of 3D depth perception.

Clearly, between FIG. 8A and FIG. 8D the amount of light transmitted through the modulator 160 is successively reduced. However, the light reduction is accompanied by a corresponding increase in exposure in response to the COMP signal, thereby producing a perception of generally uniform image intensity level. Advantageously, the apparatus 150 facilitates a smooth change in perspective from a 2D to a 3D image representation in the resulting images. The captured A and B images may be viewed using a specially adapted 3D display system, that uses special eyewear or headgear to present the different A and B images to the users left and right eyes.

Alternatively, the images may be displayed using an autostereoscopic display capable of displaying 3D image information that can be viewed without the use of special glasses or headgear.

In general, where the modulator 160 has a rectangular cross section, a rate of change in location of the centroids 182 and 184 will not vary linearly with a rate of change of area of the first and second portions 165 and 167 Accordingly, to provide a smooth transition between the images shown in FIG. 8A to FIG. 8D, the controller may be configured to cause the first and second centroids 182 and 184 to move with respect to each other at a generally constant rate to provide a smooth change in the representation of the three dimensional spatial attributes. The non-linear relation between the location of the centroids 182 and 184 and the area of the first and second portions 165 and 167 may be stored in the controller as a look-up table, for example.

LCD Modulator

Figure 9:
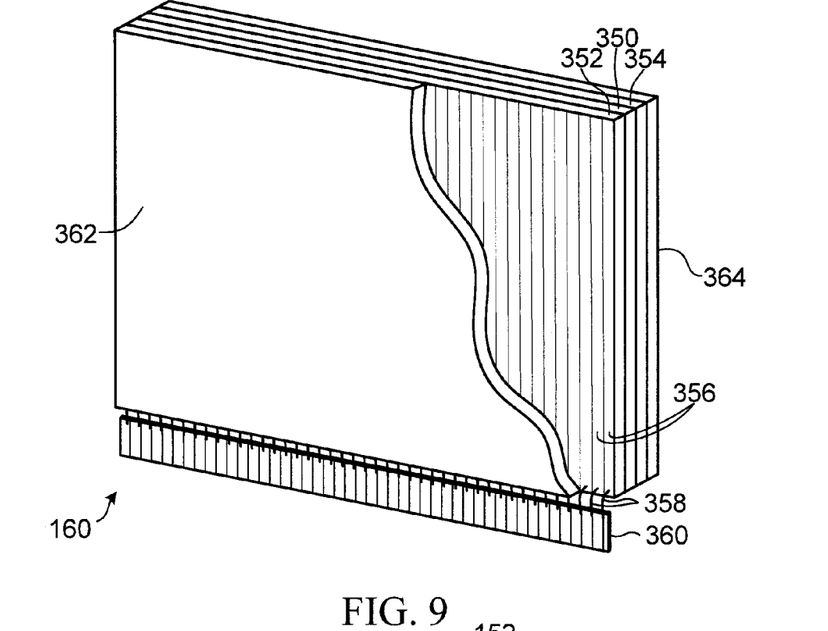
FIG. 9 is a perspective view of a liquid crystal modulator used in the optical imaging apparatus shown in FIG. 3.

The LCD modulator 160 is shown in greater detail in FIG. 9. Referring to FIG. 9, the modulator 160 includes a liquid crystal material layer 350 disposed between a first glass plate 352 and a second glass plate 354. The first glass plate 352 includes a plurality of transparent electrodes 356 arranged in columns. The electrodes 356 define an extent of each of the plurality of elements 162 shown in FIG. 3. Each electrode 356 has an associated connector 358, which may be a wire-bonded or flexible circuit connection, for example. The connectors 358 connect to a header 360, which in turn facilitates connection to the output 228 of the controller 220 shown in FIG. 6. The second glass plate 354 includes a transparent area electrode (not shown) which acts as a common electrode for all elements 162. The modulator 160 also includes a first polarizer 362, having a first linear polarization property (in this case vertical polarization). The first polarizer 362 overlays the first electrodes 356. The modulator 160 further includes a second polarizer 364 overlaying the second electrode and having a second linear polarization property (in this case horizontal polarization). In FIG. 9 the layers are not shown to scale.

The modulator driver 226 provides a drive voltage to each electrode 356 via the header 360 and connectors 358, with the common electrode acting as a ground connection. In one embodiment the drive voltage may be a 50% duty cycle square wave varying between a voltage $V^+$ and $V^-$, where the voltages are selected within a range of safe operating voltages to provide sufficient contrast between transmission and blocking of light impinging on the LCD modulator 160.

The first polarizer 362 transmits light having a vertical polarization. In this embodiment the liquid crystal material 350 is selected so that in its relaxed phase (un-actuated) the polarization of light passing through the crystal is unaffected and the second polarizer 364 thus blocks the light. When actuated by the drive voltage applied to any of the electrodes 356, a portion of the liquid crystal material underlying the electrode causes the light to undergo a 90° change in polarization, thus passing through the modulator 160. By alternately generating drive signals for first and second pluralities of the electrodes 356, the modulator 160 alternatively blocks light at the first and second portions 165 and 167 respectively. By subsequently changing a number of electrodes 356 that receive actuation signals, an extent of the first and second portions of the imaging path 152 may be varied to cause the first and second perspective viewpoints represented by the centroids 182 and 184 in FIG. 3 to change location. Advantageously, providing a sufficient number of electrodes 356 facilitates a generally smooth variation in perspective thereby preventing a visually disturbing transition from 2D to 3D imaging.

In an alternative embodiment the polarizers 362 and 364 may both be vertically polarized, such that the LCD Modulator is transmissive when no actuation voltage is applied. When actuated by the drive voltage, the liquid crystal material causes the light to undergo a 90° change in polarization thus causing elements 356 to block transmission of light.

Spatial Modulator Embodiment

Figure 10:
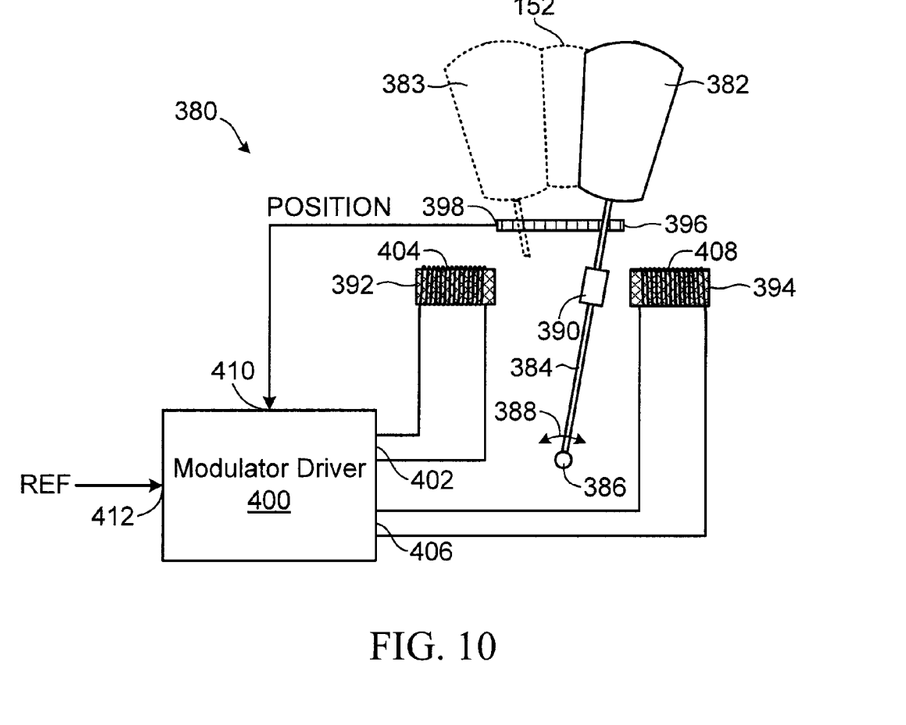
FIG. 10 is a schematic view of a spatial modulator in accordance with an alternative embodiment of the invention.

Referring to FIG. 10, in an alternative embodiment the modulator 160 shown in FIG. 3 may be implemented using the spatial modulator shown generally at 380. The spatial modulator 380 includes an opaque shutter blade 382 mounted on an arm 384. The arm 384 is mounted on a pivot 386 to provide for side-to-side motion. The arm 384 also includes a magnet 390 mounted partway along the arm. The magnet 390 is disposed between first and second electromagnets 392 and 394. The shutter blade 382, arm 384, pivot 386, and the electromagnets 392 and 394, together make up a mechanical actuator operable to produce a force for moving the shutter blade 382 from side-to-side in the direction of the arrow 388 between a first position shown at 382 and a second position shown in broken outline at 383. The first and second positions 382 and 383 define a varying extent of the first and second portions of the single imaging path 152 shown in FIG. 3.

The spatial modulator further includes a position sensor 396 located behind the arm 384. The position sensor 396 includes an output 398 for producing a position signal representative of a position of the arm 384 with respect to the position sensor. In one embodiment the position sensor 396 may be implemented using a linear photodiode array where either background stray light or illumination from a source such as a light emitting diode (not shown) casts a shadow on the array. The location of the shadowed array elements may be read out from the photodiode array at the output 398 and various interpolation methods used to determine a center location of the arm 384.

For driving the spatial modulator 380, the modulator driver 226 shown in FIG. 6 may be replaced by the modulator driver 400 shown in FIG. 10. The modulator driver 400 includes a first pair of outputs 402 for driving a coil 404 of the first electromagnet 392 and a second pair of outputs 406 for driving a coil 408 of the second electromagnet 394. The modulator driver 400 also includes an input 410 for receiving the position signal from the position sensor 396. The modulator driver 400 further includes an input 412 for receiving a reference signal representing the desired alternate positions of the arm 384. The reference signal defines an alternating target position for the arm 384 and shutter blade 382 and may be generated by the controller 220 in response to the CP signal.

The spatial modulator 380 and modulator driver 400 together implement a feedback control loop for producing alternating motion of the arm 384 and shutter blade 382 to vary an extent of blocking of the image path (shown in broken outline at 152). In operation, the reference signal received at the input 412 of the modulator driver 400 provides a target position of the arm 384, while the position signal received at the input 410 represents the actual position of the arm and may be used to produce an error signal for driving the modulator driver 400. The feedback control loop thus produces drive signals at the outputs 402 and 406 to cause the electromagnets 392 and 394 to exert drive forces on the arm 384 to move toward a desired position. Advantageously, the drive may be implemented as a push-pull driver where one of the electromagnets 392 and 394 provides an attractive force on the magnet 390, while the other of the electromagnets provides a repulsion force.

Figure 11:
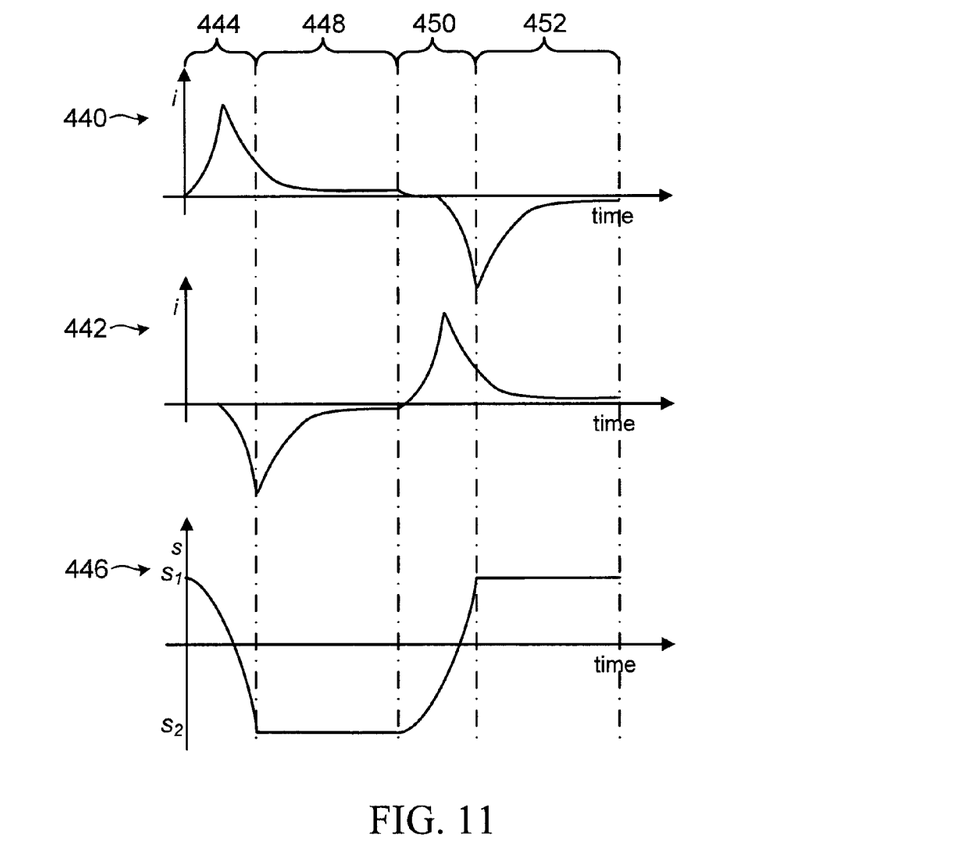
FIG. 11 is a graphical depiction of control signals for controlling the spatial modulator shown in FIG. 10.

Exemplary waveforms of a current drive provided to the coils 404 and 408 to cause the arm 384 to move toward the first electromagnet 392 are shown graphically in FIG. 11. The current waveform through the coil 404 is shown at 440 and the current waveform through the coil 408 is shown at 442. The alternating target positions provided by the reference signal REF at the input 412 are $s_1$ and $s_2$ respectively.

During a first time period 444, the error signal derived from the difference between the target position and the current position is large causing the position current 440 to increase rapidly to produce an attractive force on the arm 384. The attractive force overcomes the inertia of the arm 384 and causes the arm to accelerate away from the second electromagnet 394. The instantaneous position s of the arm 384 produced by at the position sensor output 398 is graphically depicted at 446 in FIG. 11, where a position mid-way between the electromagnets 392 and 394 is shown at s=0 on the graph and the target position is $s_2$. During the time period 444 the current 442 is initially at zero and once the arm 384 begins to accelerate, the current 442 increases rapidly to provide a decelerating force as a desired arm position $s_2$ is approached. The arm 384 comes to rest at the position $s_2$ and is held in place at this position by a holding current in each of the coils 404 and 408, which is continuously adjusted by the feedback control loop to maintain the arm 384 in the position $s_2$ for a second period of time 448. The second time period 448 provides sufficient time to complete capture of the first image.

The reference signal at the input 412 then changes defining the target position $s_1$ as the new target position. During a third time period 450, the current 442 changes polarity and increases rapidly to produce an attractive force causing the arm 384 to overcome its inertia and accelerate away from the first electromagnet 392. During the third time period 450 the current 440 is initially allowed to fall to zero and once the arm 384 begins to accelerate, the current 440 increases rapidly to provide a decelerating force as the target position $s_1$ is approached. The arm 384 comes to rest at the position $s_1$ and is held in place at this position by a holding current in each of the coils 404 and 408 which is continuously adjusted by the feedback control loop to maintain the arm 384 in the position $s_1$ for a fourth period of time 452. The fourth time period 452 provides sufficient time to complete capture of the second image.

Figure 12:
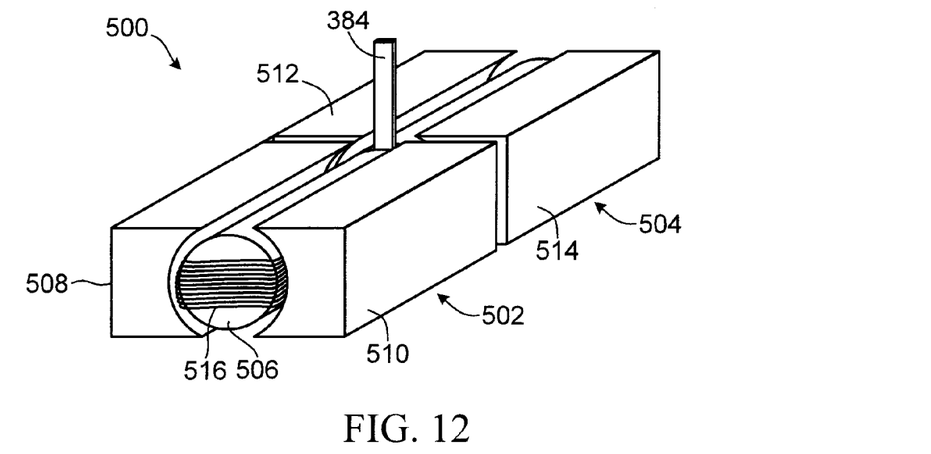
FIG. 12 is a perspective view of an alternative embodiment of an actuator for use in the spatial modulator shown in FIG. 10.

Referring to FIG. 12, an alternative embodiment of the actuator portion of the spatial modulator 380 (shown in FIG. 11) is shown generally at 500. The actuator 500 includes a motor portion 502 and a rotary position sensor portion 504. A common rotor shaft 506 extends through the motor and position sensor portions 502 and 504. The arm 384 is mounted to the shaft for side-to-side motion. In general the motor portion 502 provides a drive force for moving the arm 384, while the position sensor portion 504 provides a position signal.

In one embodiment, the motor portion 502 is implemented using a pair of magnets 508 and 510, and the sensor portion 504 is implemented using a pair of magnets 512 and 514. The shaft 506 supports an actuator coil 516 between the magnets 508 and 510. The actuator coil 516 is coupled to the modulator output 402 for receiving a drive current, which causes a torque to be generated on the coil and thus applied to the shaft 506. The sensor portion 504 also includes a pickup coil (not shown) located between the magnets 512 and 514. The pickup coil generates a current signal proportional to rotary displacement, which may be used as the position signal at the input 410. In general, the actuator 500 operates in a manner similar to an analogue meter movement.

In other embodiments, the motor portion 502 may be configured such that the shaft 506 is magnetized and the coil is wound around pole pieces (i.e. 508 and 510). Similarly, the pickup coil of the sensor portion 504 may be wound around pole pieces (i.e. 512 and 514).

Light Valve Embodiment

Figure 13:
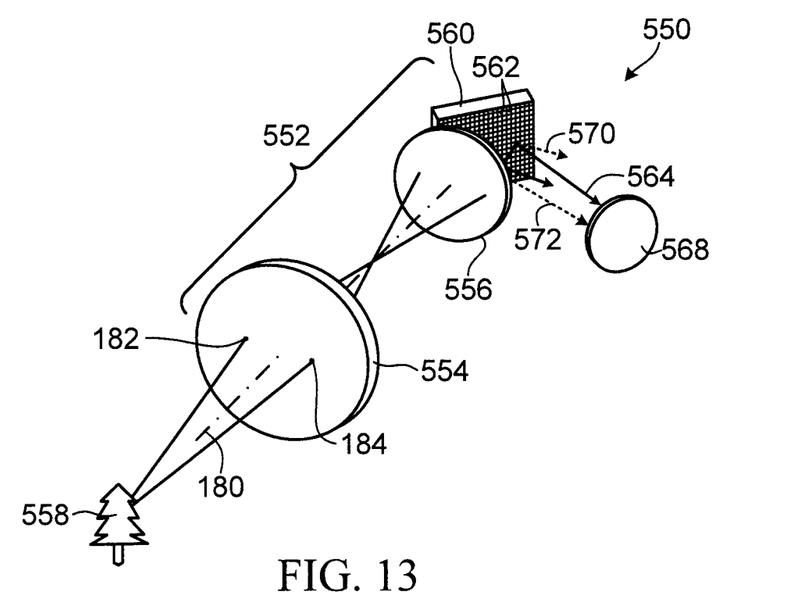
FIG. 13 is a perspective view of an alternative embodiment of an optical imaging apparatus for generating three-dimensional image information.

Referring to FIG. 13, an alternative embodiment of the optical image apparatus (shown in FIG. 3) is shown generally at 550. The apparatus 550 includes a single imaging path 552, having a first lens 554 and a second lens 556 disposed to receive light rays from an object 558 within a field of view of the first and second lenses. The apparatus 550 includes a light valve modulator 560, having a plurality of individually actuated mirror elements 562 disposed to direct a beam of light through a lens 568 when actuated. In an un-actuated state the mirror elements 562 direct the beam of light away from the lens 568. By providing drive signals to the modulator 560 to activate first and second groups of mirror elements 162, the modulator may be actuated in the alternating manner described earlier in connection with the modulator 160 shown in FIG. 3.

Other Embodiments

In an alternative embodiment, in the LCD modulator 160 shown in FIG. 9, the second polarizer 364 may be omitted to configure the modulator to selectively change the polarization of the transmitted light. Referring to FIG. 9, the first polarizer 362 only transmits light having a vertical polarization. Portions of the liquid crystal material 350 underlying un-actuated electrodes 356 thus have no effect on the polarization of the light, which is transmitted as vertically polarized light. Portions the liquid crystal material 350 underlying actuated electrodes 356 cause the light to undergo a 90° change in polarization, thus causing transmitted light to have a horizontal polarization.

Using such an alternately configured modulator in the optical imaging apparatus 150 shown in FIG. 3 results a first image having vertical polarization and a second image having horizontal polarization. Alternatively, the liquid crystal material 350 of the LCD modulator 160 may be configured to produce a first image having right circular polarized light and a second image having left circular polarized light.

The sensor 174 may be configured to simultaneously receive the respective first and second images by adding polarizing elements in front of individual sensor array elements. For example, adjacent sensor pixels may be alternately horizontally polarized and vertically polarized to provide polarization selective pixels that are sensitive to only one polarization orientation. The sensor would thus permit both the first and second images to be simultaneously received. The first and second images may be separated during readout of the array or in a separate processing step.

While specific embodiments of the invention have been described and illustrated, such embodiments should be considered illustrative of the invention only and not as limiting the invention as construed in accordance with the accompanying claims.

What is claimed is:

1. A method of generating three dimensional image information using a single imaging path having an associated field of view, the method comprising:
   selectively receiving at an image sensor first and second images through respective first and second portions of the single imaging path, said first portion having a first perspective viewpoint within the field of view and said second portion having a second perspective viewpoint within the field of view, said first and second images together being operable to represent three dimensional spatial attributes of objects within the field of view;
   changing a spacing between a centroid of said first portion of the single imaging path and a centroid of said second portion of the single imaging path to cause said first and second perspective viewpoints to change location while receiving said first and second images; and
   compensating for changes in transmission through said first and second portions of the imaging path such that while changing said spacing, an image intensity associated with each of said first and second images is maintained at a generally uniform image intensity level, wherein compensating for said changes in said transmission comprises at least one of:
   changing an exposure associated with said image sensor in response to said changes in transmission;
   changing a time that said image sensor is configured to receive light in response to said changes in transmission;
   changing a gain associated with said image sensor in response to said changes in transmission; and
   changing overall transmittance through the imaging path in response to said changes in transmission.

2. The method of claim 1, wherein selectively receiving said first and second images comprises alternately:
   blocking said first portion of the imaging path while receiving said second image; and
   blocking said second portion of the imaging path while receiving said first image.

3. The method of claim 2, wherein alternately blocking said first and second portions of the imaging path comprises selectively actuating first and second regions of an optical element located proximate an aperture plane of the image path to selectively block said first and second portions of the imaging path.

4. The method of claim 1, wherein changing said spacing comprises changing an extent of said first and second portions of the imaging path in response to a control signal.

5. The method of claim 1, further comprising generating a control signal operable to change said spacing at a constant rate to provide a smooth change in said representation of said three dimensional spatial attributes.

6. The method of claim 1, wherein changing said spacing comprises changing said spacing to transition between a three-dimensional representation and a two-dimensional representation of said objects within the field of view.

7. A method of generating three dimensional image information using a single imaging path having an associated field of view, the method comprising:
   selectively receiving at an image sensor first and second images through respective first and second portions of the single imaging path, said first portion having a first perspective viewpoint within the field of view and said second portion having a second perspective viewpoint within the field of view, said first and second images together being operable to represent three dimensional spatial attributes of objects within the field of view, wherein selectively receiving said first and second images comprises alternately:
blocking said first portion of the imaging path while receiving said second image; and
blocking said second portion of the imaging path while receiving said first image;
changing a spacing between a centroid of said first portion of the single imaging path and a centroid of said second portion of the single imaging path to cause said first and second perspective viewpoints to change location while receiving said first and second images; and
compensating for changes in transmission through said first and second portions of the imaging path such that while changing said spacing, an image intensity associated with each of said first and second images is maintained at a generally uniform image intensity level; and
alternately blocking said first and second portions of the imaging path comprises causing a blocking element located proximate an aperture plane of the image path to move between first and second positions in said image path to alternately block said first and second portions of the imaging path;
causing said blocking element to move comprises:
producing a force operable to alternately move said blocking element toward one of said first and second positions;
receiving a position signal representing a position of said blocking element; and
controlling a magnitude of said force in response to said position signal to cause the blocking element to come to rest at said one of said first and second positions.

8. A method of generating three dimensional image information using a single imaging path having an associated field of view, the method comprising:
selectively receiving at an image sensor first and second images through respective first and second portions of the single imaging path, said first portion having a first perspective viewpoint within the field of view and said second portion having a second perspective viewpoint within the field of view, said first and second images together being operable to represent three dimensional spatial attributes of objects within the field of view;
changing a spacing between a centroid of said first portion of the single imaging path and a centroid of said second portion of the single imaging path to cause said first and second perspective viewpoints to change location while receiving said first and second images; and
compensating for changes in transmission through said first and second portions of the imaging path such that while changing said spacing, an image intensity associated with each of said first and second images is maintained at a generally uniform image intensity level
wherein selectively receiving said first and second images comprises:
imparting a first polarization state to light through said first portion of the single imaging path forming said first image;
imparting a second polarization state to light through said second portion of the single imaging path forming said second image;
simultaneously receiving said first and second images at a sensor array having a first plurality of elements responsive to radiation of the first polarization state and a second plurality of elements responsive to radiation of the second polarization state; and
separating said first and second images on the basis of said first and second polarization states.

9. An apparatus for generating three dimensional image information, the apparatus comprising:
a single imaging path having an associated field of view;
an image modulator operably configured to cause first and second images to be selectively received through respective first and second portions of the single imaging path, said first portion having a first perspective viewpoint within the field of view and said second portion having a second perspective viewpoint within the field of view, said first and second images together being operable to represent three dimensional spatial attributes of objects within the field of view;
a controller in communication with said modulator, said controller being operably configured to produce a signal operable to cause said modulator to change a spacing between a centroid of said first portion of the single imaging path and a centroid of said second portion of the single imaging path to cause said first and second perspective viewpoints to change location while receiving said first and second images; and
a compensator operably configured to compensate for changes in transmission through said first and second portions of the imaging path such that while changing said spacing, an image intensity associated with each of said first and second images is maintained at a generally uniform image intensity level, wherein said single imaging path is operably configured to produce said first and second images at an image sensor and wherein said compensator is operably configured to compensate for said changes in transmission by at least one of:
changing an exposure associated with said image sensor in response to said changes in transmission;
changing a gain associated with said image sensor in response to said changes in transmission;
changing a time that said image sensor is configured to receive light in response to said changes in transmission; and
changing an overall transmittance through the imaging path in response to said changes in transmission.

10. The apparatus of claim 9, wherein said modulator is operably configured to cause a blocking element located proximate an aperture plane of the image path to move between first and second positions in said image path to alternately block said first portion of the imaging path while receiving said second image and block said second portion of the imaging path while receiving said first image and wherein said modulator comprises:
an actuator for producing a force operable to alternately move said blocking element toward one of said first and second positions;
a position sensor operably configured to produce a position signal representing a position of said blocking element; and
wherein said controller is operably configured to control a magnitude of said force in response to said position signal to cause the blocking element to come to rest at said one of said first and second positions.

11. The apparatus of claim 9, wherein said modulator is operably configured to alternately block said first portion of the imaging path while receiving said second image and block said second portion of the imaging path while receiving said first image, and wherein said modulator comprises an optical element having first and second regions, said first and second regions being operably configured to be selectively actuated to selectively block said first and second portions of the imaging path.

12. The apparatus of claim 11, wherein:
said modulator comprises a light valve having a plurality of moveable minor elements; and
said light valve is operably configured to selectively actuate first and pluralities of said moveable mirror elements to reflect light received through said respective first and second portions of the single imaging path.

13. The apparatus of claim 9, wherein said modulator is operably configured to vary the extent of said first and second portions of the imaging path in response to a control signal.

14. The apparatus of claim 9, wherein said controller is operably configured to generate a control signal operable to change said spacing at a generally constant rate to provide a smooth change in said representation of said three dimensional spatial attributes.

15. The apparatus of claim 9, wherein said controller is operably configured to change said spacing to transition between a three-dimensional representation and a two-dimensional representation of said objects within the field of view.

16. An apparatus for generating three dimensional image information, the apparatus comprising:
a single imaging path having an associated field of view;
an image modulator operably configured to cause first and second images to be selectively received through respective first and second portions of the single imaging path, said first portion having a first perspective viewpoint within the field of view and said second portion having a second perspective viewpoint within the field of view, said first and second images together being operable to represent three dimensional spatial attributes of objects within the field of view;
a controller in communication with said modulator, said controller being operably configured to produce a signal operable to cause said modulator to change a spacing between a centroid of said first portion of the single imaging path and a centroid of said second portion of the single imaging path to cause said first and second perspective viewpoints to change location while receiving said first and second images; and
a compensator operably configured to compensate for changes in transmission through said first and second portions of the imaging path such that while changing said spacing, an image intensity associated with each of said first and second images is maintained at a generally uniform image intensity level, wherein:
said modulator is operably configured to alternately block said first portion of the imaging path while receiving said second image and block said second portion of the imaging path while receiving said first image, and wherein said modulator comprises an optical element having first and second regions, said first and second regions being operably configured to be selectively actuated to selectively block said first and second portions of the imaging path;
said modulator comprises one of a liquid crystal element and a light valve;
said first region comprises a first plurality of elements and said second region comprises a second plurality of elements, said first and second pluralities of elements being selected to change said first and second portions of the imaging path; and
further comprising a modulator driver operably configured to generate actuation signals to cause a number of elements in said first and second plurality of elements to be selectively varied to change said first and second portions of the imaging path.

17. An apparatus for generating three dimensional image information, the apparatus comprising:
a single imaging path having an associated field of view;
an image modulator operably configured to cause first and second images to be selectively received through respective first and second portions of the single imaging path, said first portion having a first perspective viewpoint within the field of view and said second portion having a second perspective viewpoint within the field of view, said first and second images together being operable to represent three dimensional spatial attributes of objects within the field of view;
a controller in communication with said modulator, said controller being operably configured to produce a signal operable to cause said modulator to change a spacing between a centroid of said first portion of the single imaging path and a centroid of said second portion of the single imaging path to cause said first and second perspective viewpoints to change location while receiving said first and second images; and
a compensator operably configured to compensate for changes in transmission through said first and second portions of the imaging path such that while changing said spacing, an image intensity associated with each of said first and second images is maintained at a generally uniform image intensity level
wherein said modulator comprises:
a polarizer having first and second polarization regions operably configured to generate a first image having a first state of polarization and said second image having a second state of polarization, and
a sensor array having a first plurality of elements responsive to radiation of the first polarization state and a second plurality of elements responsive to radiation of the second polarization state, said sensor array being operable to separate said first and second images;
wherein said modulator is operably configured to:
simultaneously receive a the first and the second image; and
separate said first and second images on the basis of their states of polarization.

* * * * *